United States Patent
Vangbo et al.

(10) Patent No.: US 12,135,309 B2
(45) Date of Patent: Nov. 5, 2024

(54) SERIAL ELECTROPHORESIS

(71) Applicant: IntegenX, Inc., Pleasanton, CA (US)

(72) Inventors: Mattias Vangbo, Fremont, CA (US);
David King, Menlo Park, CA (US);
Arnaldo Barican, San Ramon, CA (US)

(73) Assignee: IntegenX, Inc., Pleasanton, CA (US)

( * ) Notice: Subject to any disclaimer, the term of this patent is extended or adjusted under 35 U.S.C. 154(b) by 0 days.

(21) Appl. No.: 18/157,274

(22) Filed: Jan. 20, 2023

(65) Prior Publication Data

US 2023/0152274 A1     May 18, 2023

Related U.S. Application Data (62) Division of application No. 16/616,339, filed as application No. PCT/US2018/033853 on May 22, 2018, now Pat. No. 11,592,421.

(Continued)

(51) Int. Cl.
*G01N 27/447* (2006.01)
*C12Q 1/6806* (2018.01)
*C12Q 1/686* (2018.01)

(52) U.S. Cl.
CPC ..... *G01N 27/44713* (2013.01); *C12Q 1/6806* (2013.01); *C12Q 1/686* (2013.01);
(Continued)

(58) Field of Classification Search
CPC ....... G01N 27/44713; G01N 27/44721; G01N 27/44778; G01N 27/44782; C12Q 1/6869; C12Q 2565/125

See application file for complete search history.

(56) References Cited

U.S. PATENT DOCUMENTS

| | | | |
|---|---|---|---|
| 9,012,236 B2 | 4/2015 | Jovanovich et al. | |
| 2004/0079640 A1 | 4/2004 | Lew et al. | |
| 2005/0130157 A1* | 6/2005 | Serwer | G01N 27/44704 |
| | | | 435/7.1 |

FOREIGN PATENT DOCUMENTS

| | | |
|---|---|---|
| CN | 104611458 A | 5/2015 |
| CN | 106282367 A | 1/2017 |

(Continued)

OTHER PUBLICATIONS

G.A. Griess, Cyclic capillary electrophoresis, Electrophoresis, 2002(23), p. 2610-17. (Year: 2002).*

(Continued)

*Primary Examiner* — C. Sun
(74) *Attorney, Agent, or Firm* — JONES ROBB, PLLC (57) ABSTRACT

A system for performing capillary electrophoresis of multiple samples comprises a capillary containing a separation medium and having inlet and distal ends and an interrogation region; a power source configured to apply voltages between inlet and distal ends; and logic to cause execution of: applying a first substantially constant forward polarity electrophoresis voltage to the capillary; before all of the first DNA fragments have passed the interrogation region, applying a reverse polarity voltage pulse to the capillary, thereby transporting at least some of the first DNA fragments in the capillary toward the capillary inlet; introducing a second sample to the capillary inlet, the second sample comprising second DNA fragments having a plurality of different sizes; and applying a second substantially constant forward polarity electrophoresis voltage to the capillary to simultaneously perform electrophoresis on the second DNA fragments and the first DNA fragments.

11 Claims, 6 Drawing Sheets

Related U.S. Application Data (60) Provisional application No. 62/509,618, filed on May 22, 2017.

(52) U.S. Cl.
CPC . *G01N 27/44791* (2013.01); *C12Q 2565/125* (2013.01); *G01N 27/44721* (2013.01)

(56) References Cited

FOREIGN PATENT DOCUMENTS

| CN | 110945138 A | 3/2020 |
|---|---|---|
| EP | 0361750 A2 | 4/1990 |
| WO | 93/05390 A1 | 3/1993 |
| WO | 2005/024411 A2 | 3/2005 |

OTHER PUBLICATIONS

International Search Report and Written Opinion dated Aug. 9, 2018, issued in PCT Application No. PCT/US2018/033853, filed May 22, 2018.
Heller et al., "DNA Separate with Field Inversion Capillary Electrophoresis", Electrophoresis, vol. 16, No. 8, Jan. 1, 1995, pp. 1423-1428.
G.A. Griess, Cyclic capillary electrophoresis, Electrophoresis, 2002(23), pp. 2610-2617. (Year: 2002).

* cited by examiner

SERIAL ELECTROPHORESIS

CROSS REFERENCE TO RELATED APPLICATIONS

This application is a divisional application of U.S. application Ser. No. 16/616,339, filed Nov. 22, 2019, which is a U.S. national stage application under 35 U.S.C. § 371(c) of International Application No. PCT/US2018/033853, filed May 22, 2018, which claims benefit of U.S. Provisional Patent Application No. 62/509,618, filed May 22, 2017, each of which is hereby incorporated by reference herein in its entirety.

INTRODUCTION

Capillary electrophoresis systems are used for separation of, e.g., PCR amplicons. In a typical workflow a sample is brought to the one end of the capillary where a small portion of the sample is injected as a plug. Typically, high voltage is applied and the charged species in the sample starts migrating inside the capillary where gel discriminates between species based on speed; the species migrate such that species with different properties become separated. The polarity of the high voltage is chosen so that species of interest are driven to migrate towards the other end of the capillary where, at some distance before the end, they are detected. The first species arrives at the location of detection at a particular time, and then the species of interest arrive later, according to their respective properties. The output from the detector reveals the time of arrival of any of the species in the population, from which information about said species, such as its size, can be discerned.

In increasing throughput of electrophoresis systems would provide many scientific and investigative benefits.

SUMMARY

The present disclosure relates to methods, systems, and apparatuses for performing capillary electrophoresis.

One aspect of the disclosure relates to a method of performing capillary electrophoresis of multiple samples. The method includes: introducing a first sample to an inlet of a capillary containing a separation medium, the first sample including first DNA fragments having a plurality of different sizes; performing electrophoresis on the first sample in the capillary, wherein the electrophoresis includes applying a first substantially constant forward polarity electrophoresis voltage to the capillary while detecting some of the first DNA fragments at an interrogation region proximate a distal end of the capillary; before all of the first DNA fragments have passed the interrogation region, applying a reverse polarity voltage pulse to the capillary, thereby transporting at least some of the first DNA fragments in the capillary toward the inlet of the capillary, and thereafter introducing a second sample to the inlet of a capillary, the second sample including second DNA fragments having a plurality of different sizes; and applying a second substantially constant forward polarity electrophoresis voltage to the capillary to simultaneously perform electrophoresis on the second DNA fragments and the first DNA fragments.

In some implementations, the method further includes introducing a plurality of internal calibrants, along with the first sample, to the inlet of the capillary, wherein each internal calibrant includes a labeled DNA fragment of distinct size. In some implementations, the first DNA fragments include amplicons from loci of STRs in a DNA source. In some implementations, the method further includes amplifying the DNA source to produce the amplicons from loci of the STRs.

In some implementations, the amplifying is performed on a system that includes the capillary.

In some implementations, the system includes a cartridge including fluidic passages and a thermocycler configured to perform polymerase chain reaction. In some implementations, introducing the second sample to the inlet of the capillary includes: introducing the second sample to an inlet region in contact with the inlet of the capillary; applying an injection forward polarity voltage pulse to create a plug of the second DNA fragments proximate the inlet of the capillary; and flushing the second sample from the inlet region.

In some implementations, applying the reverse polarity voltage pulse moves some of the first DNA fragments that had already passed the interrogation region to a position upstream of interrogation region.

In some implementations, the method further includes terminating the reverse polarity voltage pulse prior to introducing the second sample to the inlet of a capillary. In some implementations, the method further includes terminating the reverse polarity voltage pulse prior to applying the second substantially constant forward polarity electrophoresis voltage to the capillary.

In some implementations, the method further includes: (i) while performing electrophoresis on the first sample in the capillary, detecting an internal calibrant at the interrogation region; (ii) while applying the reverse polarity voltage pulse to the capillary, detecting for a second time the internal calibrant at the interrogation region; and (iii) while applying a second substantially constant forward polarity electrophoresis voltage to the capillary, detecting for a third time the internal calibrant at the interrogation region.

In some implementations, the method further includes interpreting the electrophoresis of the first DNA fragments and the second DNA fragments, wherein the interpreting includes disregarding signal obtained at the interrogation region during a period between detecting the internal calibrant for the first time and third time.

In some implementations, the method further includes before detecting all of the second DNA fragments at the interrogation region: applying a second reverse polarity voltage pulse to the capillary, thereby transporting at least some of the second DNA fragments in the capillary toward the inlet of the capillary; introducing a third sample to the inlet of a capillary, the third sample including third DNA fragments having a plurality of different sizes; and applying a third substantially constant forward polarity electrophoresis voltage to the capillary to simultaneously perform electrophoresis on the third DNA fragments and the second DNA fragments.

In some implementations, applying the reverse polarity voltage pulse moves all of the first DNA fragments that have not yet passed the interrogation region when the reverse polarity voltage pulse was applied to positions in the capillary such that when the second substantially constant forward polarity electrophoresis voltage is applied, said first DNA fragments that had not yet passed the interrogation region still have not passed the interrogation region.

In some implementations, the method further includes creating an electropherogram of the first sample by splicing together partial electropherograms of the first sample obtained before and after applying the reverse polarity voltage pulse.

In some implementations, splicing together includes removing data obtained after a reference point in a first partial electropherogram obtained before applying the reverse polarity voltage pulse and removing data obtained before the reference point in a second partial electropherogram obtained after applying the reverse polarity voltage pulse. In some implementations, the method further includes identifying the reference point by identifying an electropherogram peak associated with the reference point.

Another aspect of the disclosure relates to a method of performing capillary electrophoresis of multiple samples. The method includes: initiating electrophoresis of a first sample in a capillary containing a separation medium, the first sample including first DNA fragments having a plurality of different sizes; conducting steady-state transport of first DNA fragments from the first sample by applying a substantially constant forward polarity electrophoresis voltage to the capillary; before completing electrophoresis of the first sample, halting application of the substantially constant forward polarity electrophoresis voltage and thereby interrupting the steady-state transport of the first DNA fragments in the capillary; applying a reverse polarity voltage to the capillary to drive transport of the first DNA fragments toward an inlet of the capillary; halting application of the reverse polarity voltage; introducing a second sample to an inlet region in contact with the capillary inlet, wherein the second sample includes second DNA fragments having a plurality of different sizes; applying an injection forward polarity voltage pulse to create a plug of the second DNA fragments in the capillary, proximate the capillary inlet; applying a second substantially constant forward polarity voltage to cause steady-state transport of both the first DNA fragments and the second DNA fragments in the capillary; and interrogating the first DNA fragments and the second DNA fragments as they reach an interrogation region proximate a distal end of the capillary.

A further aspect of the disclosure relates to a system for performing capillary electrophoresis of multiple samples. The system includes: (a) a capillary containing a separation medium and having inlet and distal ends; (b) an inlet in communication with the capillary inlet and configured to receive samples containing DNA fragments having a plurality of different sizes; (c) an interrogation region configured to detect DNA fragments moving through the capillary; (d) a power source configured to apply forward and reverse polarity voltages between inlet and distal ends of the capillary; and (e) logic. The control logic is configured for directing the following operations: introducing a first sample to the capillary inlet, the first sample including first DNA fragments having a plurality of different sizes; performing electrophoresis on the first sample in the capillary by applying a first substantially constant forward polarity electrophoresis voltage to the capillary while detecting some of the first DNA fragments at the interrogation region; before all of the first DNA fragments have passed the interrogation region, applying a reverse polarity voltage pulse to the capillary, thereby transporting at least some of the first DNA fragments in the capillary toward the capillary inlet; thereafter introducing a second sample to the capillary inlet, the second sample including second DNA fragments having a plurality of different sizes; and applying a second substantially constant forward polarity electrophoresis voltage to the capillary to simultaneously perform electrophoresis on the second DNA fragments and the first DNA fragments.

In some implementations, the system further includes a chassis enclosing the capillary, the inlet region, the interrogation region, the power supply, and the logic.

In some implementations, the system further includes a chassis enclosing the capillary, the inlet region, the interrogation region, and the power supply, but not the logic.

In some implementations, the system further includes logic for creating an electropherogram of the first sample by splicing together partial electropherograms of the first sample obtained before and after applying the reverse polarity voltage pulse. In some implementations, the system further includes the logic is further configured to direct amplifying the DNA source to produce amplicons from loci of the STRs. In some implementations, the system further includes a cartridge including fluidic passages and a thermocycler configured to perform polymerase chain reaction.

In some implementations, the system further includes the logic is further configured to direct the introduction of the second sample to the inlet of the capillary by: introducing the second sample to an inlet region in contact with the inlet of the capillary; applying an injection forward polarity voltage pulse to create a plug of the second DNA fragments proximate the inlet of the capillary; and flushing the second sample from the inlet region. In some implementations, the logic is further configured to terminate the reverse polarity voltage pulse prior to introducing the second sample to the inlet of a capillary.

In some implementations, the logic is further configured to terminate the reverse polarity voltage pulse prior to applying the second substantially constant forward polarity electrophoresis voltage to the capillary.

In some implementations, the logic is further configured to direct the following operations: (i) while performing electrophoresis on the first sample in the capillary, detecting an internal calibrant at the interrogation region; (ii) while applying the reverse polarity voltage pulse to the capillary, detecting for a second time the internal calibrant at the interrogation region; and (iii) while applying a second substantially constant forward polarity electrophoresis voltage to the capillary, detecting for a third time the internal calibrant at the interrogation region. In some implementations, the logic is further configured to direct the following operation: interpreting the electrophoresis of the first DNA fragments and the second DNA fragments, wherein the interpreting includes disregarding signal obtained at the interrogation region during a period between detecting the internal calibrant for the first time and third time.

In some implementations, the logic is further configured to direct the following operation before detecting all of the second DNA fragments at the interrogation region: applying a second reverse polarity voltage pulse to the capillary, thereby transporting at least some of the second DNA fragments in the capillary toward the inlet of the capillary; introducing a third sample to the inlet of a capillary, the third sample including third DNA fragments having a plurality of different sizes; and applying a third substantially constant forward polarity electrophoresis voltage to the capillary to simultaneously perform electrophoresis on the third DNA fragments and the second DNA fragments.

In some implementations, the logic is further configured to direct the following operation: creating an electropherogram of the first sample by splicing together partial electropherograms of the first sample obtained before and after applying the reverse polarity voltage pulse. In some implementations, splicing together includes removing data obtained after a reference point in a first partial electropherogram obtained before applying the reverse polarity voltage pulse and removing data obtained before the reference point in a second partial electropherogram obtained after applying the reverse polarity voltage pulse.

In some implementations, the logic is further configured to direct the following operation: identifying the reference point by identifying an electropherogram peak associated with the reference point.
Description

TERMINOLOGY

Every embodiment of the disclosure may optionally be combined with any one or more of the other embodiments described herein which are consistent with that embodiment.

Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values. In certain embodiments, the term "about" or "approximately" means within 10% or 5% of the specified value.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "sample", as used herein, refers to a sample containing biological material. A sample may be, e.g., a fluid sample (e.g., a blood sample) or a tissue sample (e.g., a cheek swab). A sample may be a portion of a larger sample. A sample can be a biological sample having a nucleic acid, such as deoxyribonucleic acid (DNA) or ribonucleic acid (RNA), or a protein. A sample can be a forensic sample or an environmental sample. A sample can be pre-processed before it is introduced to the system; the preprocessing can include extraction from a material that would not fit into the system, quantification of the amount of cells, DNA or other biopolymers or molecules, concentration of a sample, separation of cell types such as sperm from epithelial cells, concentration of DNA using an Aurora system (Boreal Genomics) or bead processing or other concentration methods or other manipulations of the sample. A sample can be carried in a carrier, such as a swab, a wipe, a sponge, a scraper, a piece punched out a material, a material on which a target analyte is splattered, a food sample, a liquid in which an analyte is dissolved, such as water, soda. A sample can be a direct biological sample such as a liquid such as blood, semen, saliva; or a solid such a solid tissue sample, flesh or bone.

The disclosed embodiments can also be applied to process and analyze a sample that has been previously preprocessed, for example, by extraction of DNA from large object such as a bed sheet or chair and other processing which may include quantification of DNA concentration, cell concentration, or other manipulations before input of the pre-processed sample into the sample cartridge.

DETAILED DESCRIPTION

A limitation on the throughput on an electrophoresis system is how often a capillary can accept a new sample. Classically, a next sample is not injected until all its species of interest in a first sample have migrated past the location of detection. In, e.g., a typical STR analysis the time until the first species arrives at the detector is about one third the time until the slowest species arrives, hence during a third of the time there is no information of interest collected.

One might consider using a system that interrupts the ongoing migration of a sample and injects the next sample into the capillary such that when the migration is resumed, the fastest species of the next sample do not reach the location of detection until the slowest species of the first sample has already arrived. In that way the time when there are no species of interest arriving at the detector is minimized. However, in interrupting the migration of the first sample the important timing information collected at the location of detection is compromised. In particular the injection itself involves applying a sequence of voltages. Further, there is a perception that some fragments from a sample might be retained in the capillary, so it is safe to fully clear a current sample before introducing a next sample.

This approach could be error prone due to various uncharacterized system time constants for, e.g., controlling and detecting high voltage, thermal time constants related to the joule heating in the capillary from applying the high voltage, as well as any non-linearity of the migration speed with the voltage applied. As explained below, such challenges can be addressed by compensating for the initial high voltage pulse (often referred to as an injection pulse) and other variations associated with introducing the next sample.

Apparatus

Figure 1A:
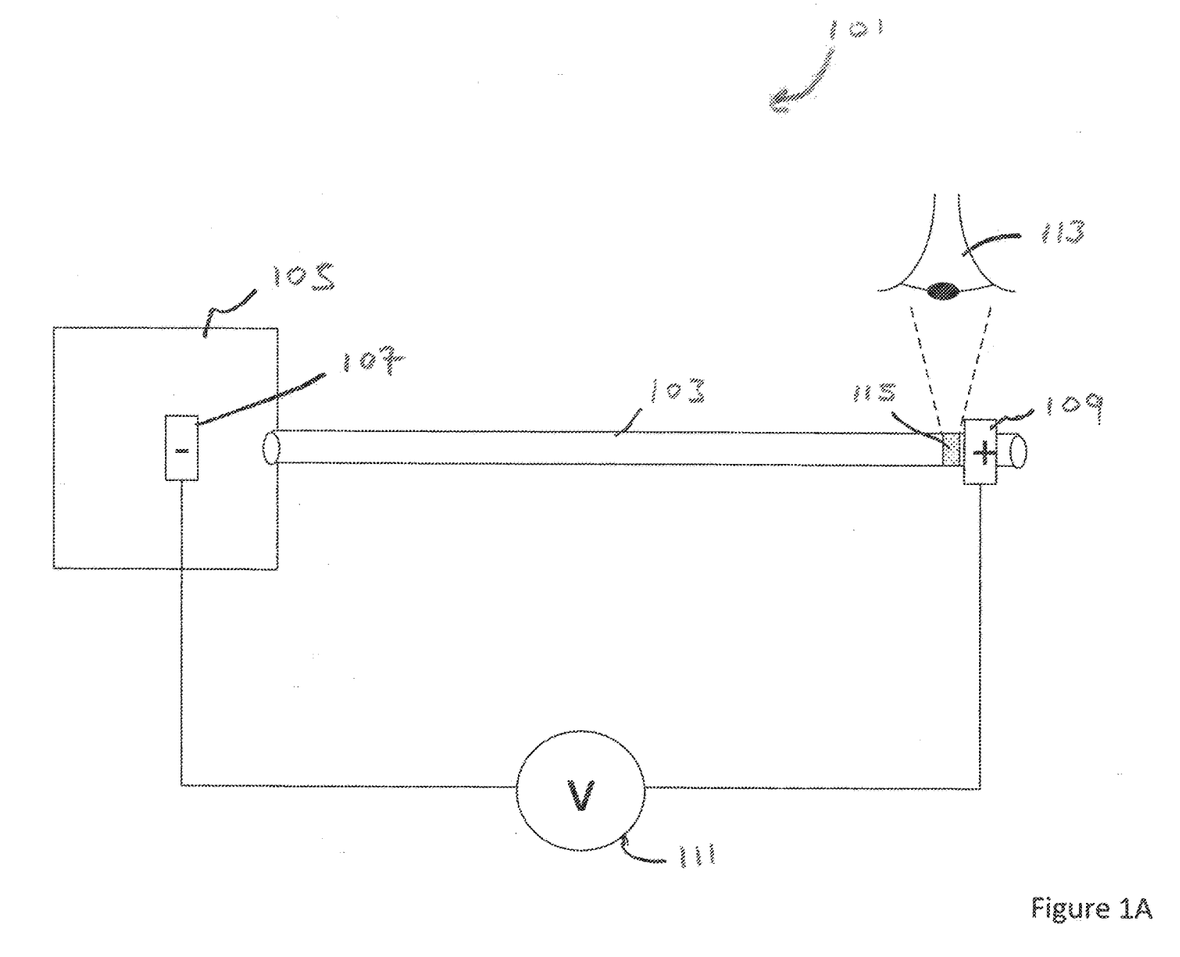
FIG. 1A is a block diagram depicting electrophoresis apparatus suitable for use with the processes described herein.
Figure 2:
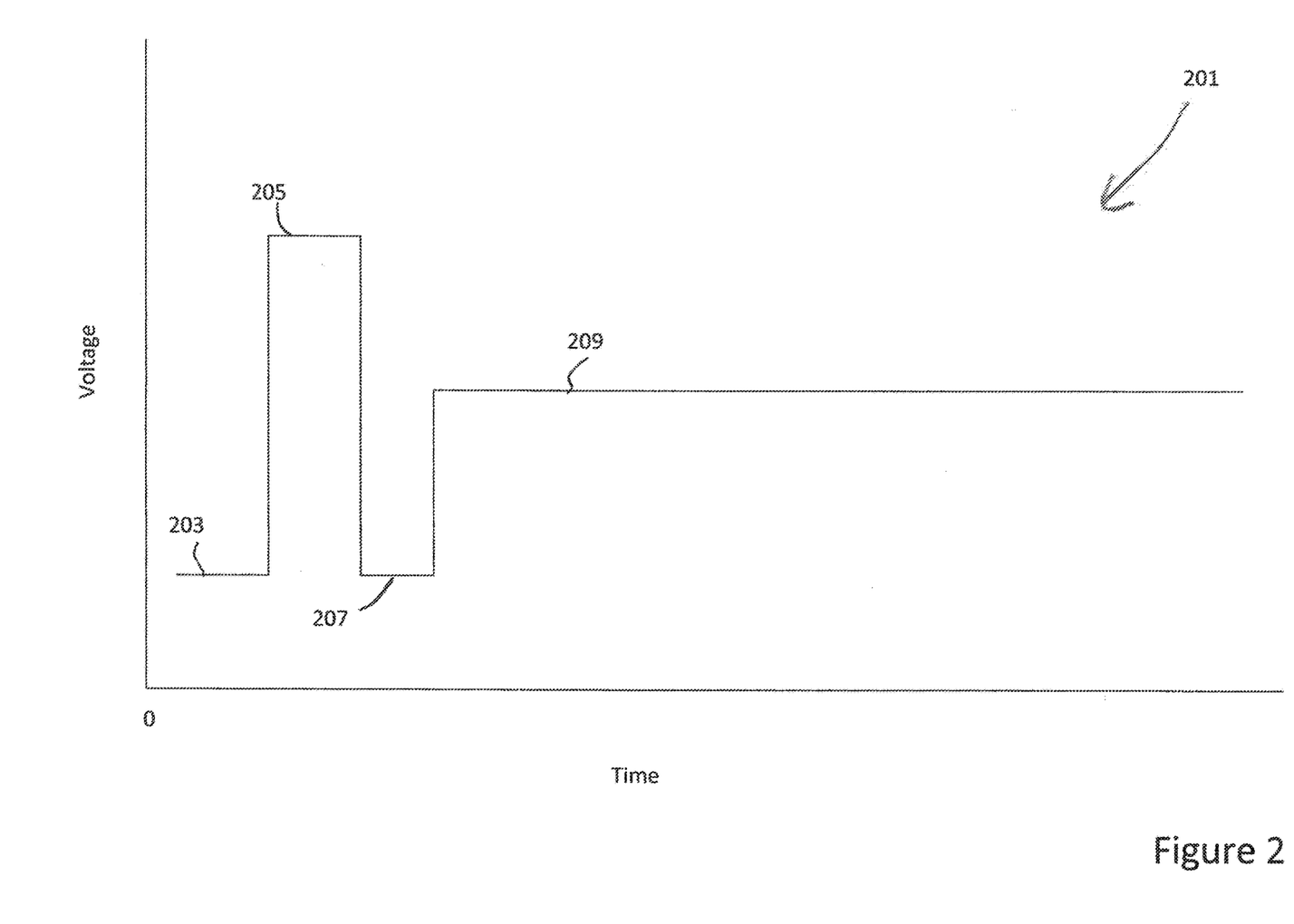
FIG. 2 is a timing diagram depicting a conventional electrophoresis process.

In certain embodiments, the relevant components and operation of the apparatus are fairly simple and are described in connection with FIGS. 1A and 2. FIG. 1A presents a block diagram of the apparatus and FIG. 2 provides a conventional electropherogram timing diagram.

As shown in FIG. 1A, an electrophoresis apparatus 101 includes a capillary with gel 103 and an inlet region 105 (e.g., an inlet chamber) at the entrance of the capillary. During operation, a DNA sample is provided to inlet region 105. The sample may be provided in a buffer solution. In the inlet region 105, the sample contacts the gel at a proximal end of the capillary. The apparatus 101 also includes electrophoresis electrodes 107 and 109. As shown, electrode 109 is provided with a positive charge and disposed at a distal end of capillary 103, while electrode 107 is provided with a negative charge and disposed at the proximal end of the capillary. This polarity is sometimes referred to as a "forward" electrophoresis voltage; the absolute magnitudes of the potentials at the electrodes are less relevant than the relative difference in their potentials. A power source 111 is configured to apply one or more defined voltage levels to one or both of electrodes 107 and 109. The power source is connected by electrically conductive lines and/or other circuit elements to the electrodes. Finally, electrophoresis apparatus 101 includes a detection system 113 configured to detect sample species passing through an interrogation region 115 near the distal end of capillary 103. The detection system detects signal emitted by species in the interrogation region. In certain embodiments, the detection system detects fluorescent signal emitted by species. In some implementations, the apparatus includes components not directly connected to performing electrophoresis. These may include a cartridge that includes fluidic passages and a thermocycler configured to perform polymerase chain reaction. Examples of apparatus, modules, and systems suitable for use with the present disclosure are presented in U.S. Pat. No. 8,894,946, issued Nov. 25, 2014, which is incorporated herein by reference in its entirety.

Figure 1B:
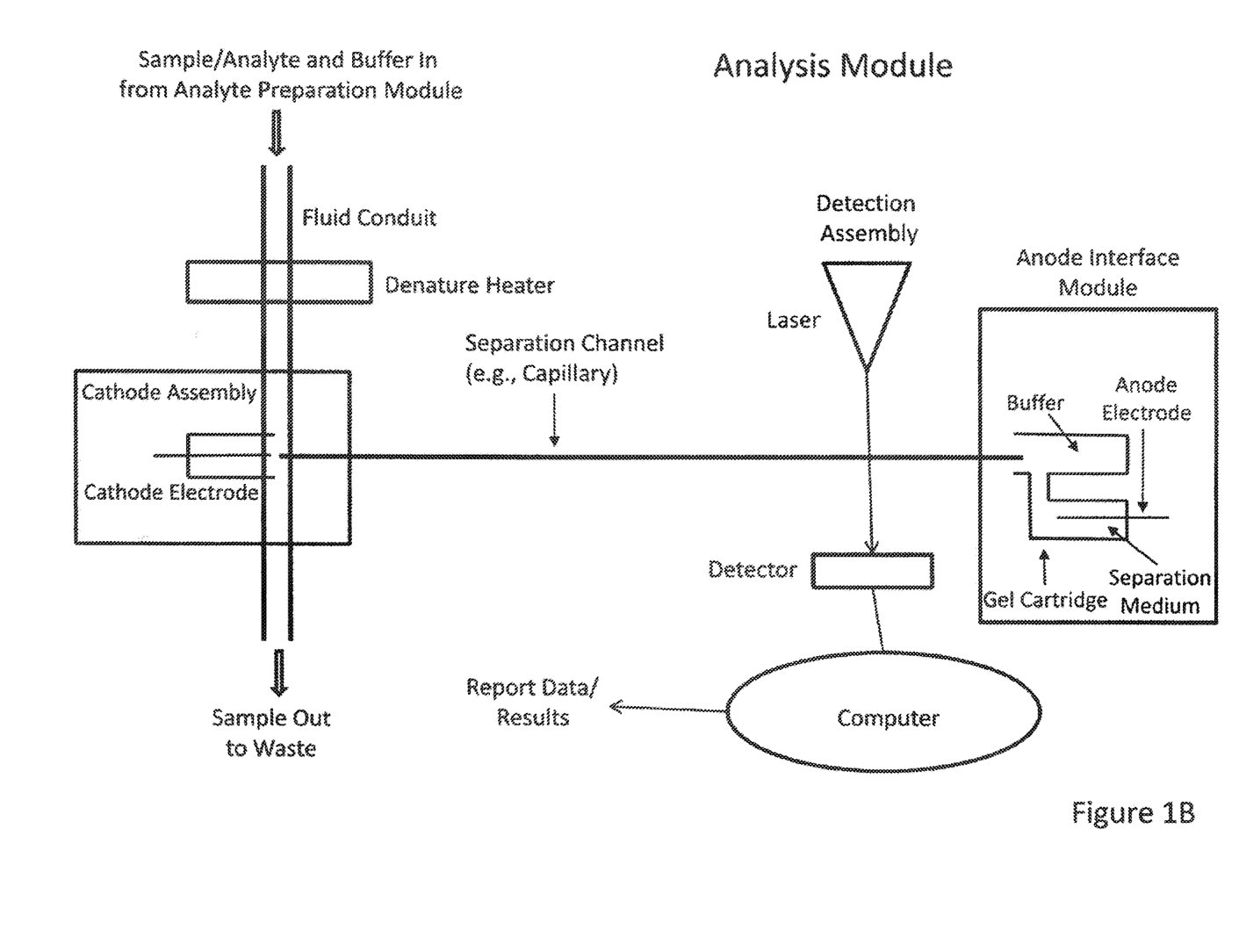
FIG. 1B is a schematic illustration of an analysis module useful in the systems described herein.

In certain embodiments, a capillary electrophoresis system is part of an analysis and detection module illustrated in FIG. 1B. In the depicted embodiment, a sample (e.g., amplified DNA or controls) and buffer (e.g., electrophoresis buffer) flow through a fluidic conduit, such as a tube, from an analyte preparation module in a path that can include a denature heater, a cathode assembly for injecting analyte into a capillary, and out to waste. A denature heater heats fluid containing DNA and denatures strands in double stranded DNA. The cathode assembly can include an electrode, such as a forked electrode, connected to a source of voltage. When a sample to be analyzed is positioned for injection, the electrode can provide voltage to inject the analyte into the capillary. The capillary is filled with a separation medium, such as linear polyacrylamide (e.g., LPA V2e, available from IntegenX Inc., Pleasanton, Calif.). The capillary ends are electrically connected to a voltage source, e.g., two electrodes, operated as an positive electrode (labelled as anode) and a negative electrode (labelled as cathode), and capable of being powered in the reverse direction e.g., the negative electrode becomes the positive electrode when a power source applies a positive potential to the electrode. Separated analyte is detected with a detection module. The detection module can employ, for example, a laser and a detector, such as a CCD camera, CMOS, photomultiplier, or photodiode. Any of these may be disposed to detect passing DNA fragments in an interrogation region. The anode assembly (e.g., anode cartridge interface) can include an anode in electrical connection with the capillary and a source of voltage. The anode assembly also can include a source of separation medium and a source of pressure for introducing separation medium into a capillary. The anode assembly can include electrophoresis buffer. The separation medium and/or the electrophoresis buffer can be included in an anode cartridge. The anode cartridge can be configured for removable insertion into the anode assembly. It can contain separation medium and/or electrophoresis buffer sufficient for one or more than one run.

In certain embodiments, the capillary electrophoresis assembly includes an injection assembly that can include a denature assembly, a cathode assembly; a capillary assembly; an anode assembly; a capillary filling assembly for filling a capillary with separation medium; a positioning assembly for positioning an analyte (or sample) for capillary injection; and a power source for applying a voltage between the anode and the cathode.

The capillary electrophoresis system can include one or more capillaries for facilitating sample or product separation, which can aid in analysis. In some embodiments, a fluid flow path directs a sample or product from the cartridge to an intersection between the fluid flow path and a separation channel. (See FIG. 1B) The sample is directed from the fluid flow path to the separation channel, and is directed through the separation channel with the aid of an electric field, as can be generated upon the application of an electrical potential across an anode and a cathode of the system (see below). U.S. Patent Publication No. 2011/0005932 ("UNIVERSAL SAMPLE PREPARATION SYSTEM AND USE IN AN INTEGRATED ANALYSIS SYSTEM"), which is incorporated herein by reference in its entirety, provides examples of electrophoresis capillaries for use in analysis, as may be used with systems herein. The capillary can be inserted into the fluidic conduit for fluidic and electric communication.

A cathode also can be in electric communication with the capillary through an electric communication with fluid in the fluidic conduit. The cathode can be disposed in the fluidic conduit near the connection with the capillary. For example the cathode can be positioned opposite the point at which the capillary connects with the fluidic conduit (e.g., neither upstream nor downstream of the connection). This can aid injection of the sample into the capillary and/or to provide voltage for the electrophoresis run. In certain embodiments, the cathode can comprise a forked electrode in which one fork is positioned upstream and one fork is positioned downstream of the point of connection of the capillary and the fluidic conduit. In other embodiments, the cathode comprises both a forked electrode and a third electrode positioned near the connection between the fluidic conduit and the capillary.

An electrophoresis sample (e.g., amplification products) can be prepared for injection into a separation channel (e.g., a capillary) by any suitable method. As an example, field-amplified stacking (FAS) can be performed by positioning in an electrophoresis sample channel a diluted mixture comprising the sample of lower salt concentration or lower ionic strength between areas comprising an electrophoresis buffer of higher salt concentration or higher ionic strength. As another example, a bolus of a material (e.g., air) can be positioned downstream of the sample in the sample channel, wherein the material has an electrical conductivity that differs from the electrical conductivity of the electrophoresis buffer or the sample, as described below. When the sample is positioned across the separation channel, the sample can be electrokinetically injected into the separation channel at an appropriate voltage (e.g., about 3 kV to about 5 kV, or about 4 kV) over an appropriate amount of time (e.g., about 10 sec to about 20 sec, or about 15 sec).

The system may include a device for regulating the temperature of the electrophoresis capillary or capillaries. The capillary may be disposed in an electrically insulating circuit board that has a generally curved path or a substantially straight path for placement of the capillary. In some embodiments, the capillary is provided in a curvilinear path, such as, e.g., a generally S-shaped path. The path can be distributed into a plurality of sections. Each of the sections separately regulates the temperature in a portion of the capillary in thermal communication with the section. Temperature may be regulated with the aid of resistive heating, though other temperature control elements (e.g., heating element and/or cooling element), or devices may be used. Temperature can be measured with the aid of a temperature sensing device, such as a thermocouple, a thermistor or a resistive temperature device (RTD) in each section. Each of the different sections includes an electrical path that traverses the capillaries of each section. In some cases, the electrical path traverses back and forth (e.g., in a serpentine shape in that section). The electrical path includes one or more temperature control elements (e.g., heating elements and/or cooling elements) (e.g., resistive heaters) for providing heat to the capillary.

A thermal sensor is in contact with each of the separately thermally regulated areas or sections of the path. Examples of temperature sensors are thermistors or other temperature-varying resistance, or thermocouples or other temperature-varying voltage source. In some cases, the temperature data of the separately thermally regulated sections is not gathered by discrete temperature sensor, but by the electrical paths themselves such as by the resistances of the electrical paths. External temperature sensors may also be used.

Electrophoresis Process

Electrophoresis is generally conducted according a defined protocol, which may be represented via a timing diagram. See diagram 201 of FIG. 2. Initially in the electrophoresis process, a sample is introduced to system. See sample introduction portion 203 of timing diagram 201. The sample may be obtained from any of various sources such as crime scene samples (e.g., bone, teeth), bodily fluid (sputum, urine, blood, semen, hair, etc.), and buccal swab samples taken from the cheek or a known individual. In some embodiments, the sample is preprocessed according to a standard such as described in US Patent Application Publication 2016/0116439, published Apr. 28, 2016 (Kindwall et al.), which is incorporated herein by reference in its entirety. Preprocessing may include operations such as lysis, DNA extraction, and DNA amplification. In some applications, preprocessing includes amplifying DNA to produce the amplicons from loci of the STRs. In some implementations, the first DNA fragments undergoing electrophoresis are amplicons from loci of STRs in a DNA source.

In some implementations, before introduction to the inlet region (e.g., region 105 of FIG. 1A), the sample's DNA fragment concentration is adjusted to a standard concentration and/or a standard volume. Once in the inlet region, the sample DNA fragments in a buffer may contact an entrance to the capillary (e.g., capillary 103 of FIG. 1A), but the sample does not significantly enter the capillary gel. After the sample is loaded into a chamber or other region at the entrance of the capillary, a large magnitude injection voltage pulse is applied to drive the DNA from the inlet region into the gel, where all the DNA in the sample forms a plug near the entrance. See the injection voltage portion 205 of timing diagram 201.

The injection pulse is applied across two electrodes such as electrodes 107 and 109 in FIG. 1A, one at the inlet of the capillary and the other at the outlet of the capillary (distal end). As mentioned, for negatively charged analytes such as DNA, the more positive potential is applied to the outlet and the more negative potential is applied to the inlet.

After the injection voltage pulse ends—e.g., the voltage goes to zero magnitude—the sample is flushed out of the inlet region and a buffer is introduced into the region. The buffer can serve as a medium to transport of the DNA fragments through the length of the capillary. See the buffer introduction portion 207 of timing diagram 201.

After the buffer is introduced to the inlet region, a new electrophoresis voltage, called the main electrophoresis voltage, is applied and maintained for the duration of the electrophoresis process. Typically, it has a lower magnitude and longer duration than the injection voltage pulse. See the electrophoresis voltage application portion 209 of timing diagram 201.

The electrophoresis voltage sets up the steady-state transport of buffer and DNA fragments through the capillary. The steady-state flow ensures that different alleles, which have different lengths, reach the interrogation region near the distal end of the capillary at reasonably predictable times.

Conventional STR electrophoresis employs many internal calibrants, where each calibrant is a DNA fragment of a defined size labeled with a particular dye that is unique to the internal calibrants. Using a combination of calibrant detection and sample fragment travel time, conventional systems determine the fragment size of the allele being read at the interrogation region.

Further details of some embodiments of an electrophoresis process are presented in U.S. Pat. No. 8,894,946, previously incorporated herein by reference.

Staggered Electrophoresis

The disclosed system and associated method sequentially process multiple samples in a single gel, e.g., in a single capillary. For reasons mentioned above, putting multiple samples in a single gel was viewed as an unacceptable practice. There is a perception that some DNA fragments could remain stuck in the gel after a prior sample is processed, and that the fragments remaining in the gel could interfere with the next sample subjected to electrophoresis. However, in embodiments of this disclosure, this has not been observed to be problem.

1. Staggered Introduction of Samples

Two or more samples are processed serially. As indicated elsewhere herein, this disclosure refers to two sequentially processed samples, a "current" sample and a "next" sample. The samples are introduced such that the next sample is introduced into a gel before the current sample completes electrophoresis in the same gel. In other words, the next sample is introduced to the gel before all nucleic acid fragments in the current sample have passed through the capillary's interrogation region. However, the next sample is not introduced so early that its fastest moving fragment can catch the slowest moving fragment of the current sample. In other words, there is no overlap between the interrogation of fragments of the current sample and fragments of the next sample. However, because the next sample is introduced before electrophoresis of the current sample is complete, the sample throughput is increased compared to a case in which the next sample is introduced only after the prior sample has run to completion.

This staggered introduction, and particularly the fact that the next sample is introduced before the prior sample is run to completion, introduces certain technical challenges. Notably, the introduction of the next sample requires prematurely ending application of the electrophoresis voltage for the current sample. It also requires applying an injection high-voltage pulse for the next sample. Both of these variations from the constant electrophoresis voltage affect the transport time of the DNA fragments of the current sample and can make timing-based interrogation of the current sample unreliable. To reduce reliance on transport time, one could design a system with many additional internal calibrants, but these are expensive.

The potential problems of staggered electrophoresis will now be explained in more detail. As explained, after a new sample is loaded into the inlet region at the entrance of the capillary, a large magnitude injection voltage pulse is applied across the electrophoresis electrodes to inject the DNA from the sample into the gel. Through this injection voltage pulse, the DNA fragments of the sample form a narrow width plug near the entrance of the capillary. After the voltage pulse ends—e.g., the voltage goes to zero or near zero magnitude—a buffer is introduced into the region. An electrophoresis running voltage is then applied and maintained for the duration of the electrophoresis process. This electrophoresis running voltage sets up the steady-state transport of buffer and DNA fragments through the capillary. The steady-state flow ensures that different alleles, which have different lengths, reach the interrogation region at the distal end of the capillary at reasonably predictable times.

However, there are nonlinearities in how the gel interacts with nucleic acid fragments of particular lengths. In particular, the travel rate is not a linear function of fragment size. For any given gel, there are certain well-characterized regions of fragment size where there is a reasonably strong deviation from linearity. To address this challenge, conventional electrophoresis employs many internal calibrants, where each calibrant is a fragment of a defined size labeled with a particular dye that is unique to the internal calibrants. Using a combination of calibrant detection and sample fragment travel time, conventional systems determine the fragment size of the allele being read at the interrogation region. For a given process design, the number of internal calibrants is minimized to reduce cost.

Note that the number and pattern of spacings between adjacent internal calibrants are well-defined and can be used as a ruler for determining the length of any allele fragments passing through the interrogation region. To account for the above-mentioned non-linearities, the internal calibrants are not evenly spaced.

Because electrophoresis analysis relies on steady-state flow of one sample, introduction of a second sample before the first sample completes can introduce errors. This is because the second sample requires a period of no applied voltage when the second sample is loaded. It also requires an introductory voltage pulse and a second period of no applied voltage when the sample is flushed. All of this causes the first sample to depart from steady-state flow. In theory, the first sample could be processed with such deviations from steady-state flow. This would be possible by employing many additional internal calibrants. In other words, the spacing between successive calibrants would be consistently small enough to provide the resolution necessary to uniquely identify all sample fragments of interest without relying on transport time.

Unfortunately, internal calibrants are costly and using many of them significantly adds to the cost of sample analysis. Therefore, in various embodiments, few, if any, additional calibrants are used. In certain embodiments, the internal calibrants span a fragment size range of between about 20 base pairs and 1000 base pairs, or between about 50 base pairs and 700 base pairs, or between about 100 base pairs and about 500 base pairs.

To recap, certain disclosed embodiments employ a staggered introduction of successive electrophoresis samples and they do so in a manner that does not use more than a defined and relatively low number or density of internal calibrants. In embodiments, with this constraint, the system compensates for the non-steady transport of fragments near the interrogation region when the next sample is started. In some cases, the system accomplishes this by applying a reverse voltage pulse prior to introduction of the next sample.

2. Reverse Polarity Voltage Pulse

Because some embodiments use only limited numbers internal calibrants, the electrophoresis runs must rely on the respective transport times of the DNA fragments travelling through the capillary to reach the interrogation region. This means that the process must compensate for non-steady-state transport of the DNA fragments through the capillary. As explained, the non-steady-state transport is caused by variations in the electrical field applied to the capillary during the initial stages the next sample introduction and electrophoresis.

In various embodiments, the electrophoresis system compensates for non-steady-state transport by stopping electrophoresis before the current sample has been completely analyzed and before the next sample is introduced, and applying a reverse polarity voltage pulse to the capillary. In other words, a potential is applied to the electrodes such that the potential of the electrode at the distal end of the capillary is relatively negative compared to the potential of the electrode at the proximal end of the capillary. This runs the DNA fragments in reverse direction, effectively backing them up in the capillary, so that when the next sample starts up—at which time the system produces the required large voltage variations such as the injection pulse—the DNA fragments already in the capillary must move forward by some distance before regaining their positions prior to the reverse polarity pulse. Thus, during the initial phases of the next sample run, the DNA fragments are rerun in the forward direction, retracing a portion of their migration through the capillary. By the time these fragments reach the interrogation region, they are travelling under the influence of the running electrophoresis voltage applied for the next sample. In other words, they are travelling under steady-state conditions. In some embodiments, by the time the fragments reach the point at which the reverse polarity voltage pulse was applied, they are travelling under the influence of the running electrophoresis voltage.

In one embodiment, under reverse polarity, fragments of the current sample are moved backward a sufficient distance so that the leading edge of the electropherogram, after the next sample injection and return to running electrophoresis voltage, overlaps the back edge of the electropherogram pre-stop, so that the pre- and post-stop electropherograms can be stitched together.

The reverse pulse is applied in a manner that ensures that detection of fragments from the next sample do not interfere with the electropherogram for the current sample. In certain embodiments, the reverse pulse is timed so that the fastest fragment of the next sample does not catch the slowest fragment of the current sample at the interrogation region. This may be ensured by starting the reverse pulse only after a defined fraction of the DNA fragments from the current sample are detected and/or running the reverse pulse for a limited duration (and/or at a limited magnitude). In certain embodiments, a current sample is run to approximately 20 to 80% of completion before the next sample is introduced. In certain embodiments, a current sample is run to approximately 50 to 80% of completion before the next sample is introduced.

Considering the DNA fragments in total in the current sample, all fragments were either (a) transported and detected prior to the reverse polarity pulse using normal electrophoresis processing (i.e., they were transported all the way through the capillary to the interrogation region using the steady running electrophoresis voltage without being exposed to the start-up conditions for the next sample), or (b) subjected to unsteady voltages from the next sample start up, but only while they are located in positions upstream from their positions when they were exposed to the reverse polarity voltage pulse. When the reverse polarity pulse is large enough, the second type of fragments regain steady transport well before reaching the interrogation region, thereby providing some overlap in time between the pre-stop and post-stop electrophoresis detection data. This allows the system to create a composite electropherogram in which distortions caused by stopping, reversing, injecting, and re-running are effectively eliminated, or do not significantly interfere with detection of peaks across the composite electropherogram.

In some implementations, the resulting interrogation data is manipulated by removing all peaks generated during a time frame starting with or just before the initiation of the reverse polarity voltage pulse and ending when the DNA fragments regain the positions they attained when the reverse polarity pulse was applied. In other embodiments, electropherogram data is simply not collected during the reverse pulse and/or during the initial phases of the next sample (e.g., injection). When the electropherogram data from before the reverse pulse is aligned with electropherogram data after the injection of the next sample, the process is sometimes referred to as splicing two electropherogram traces, and it will be described in more detail with reference to FIGS. 4A and B.

Figure 3:
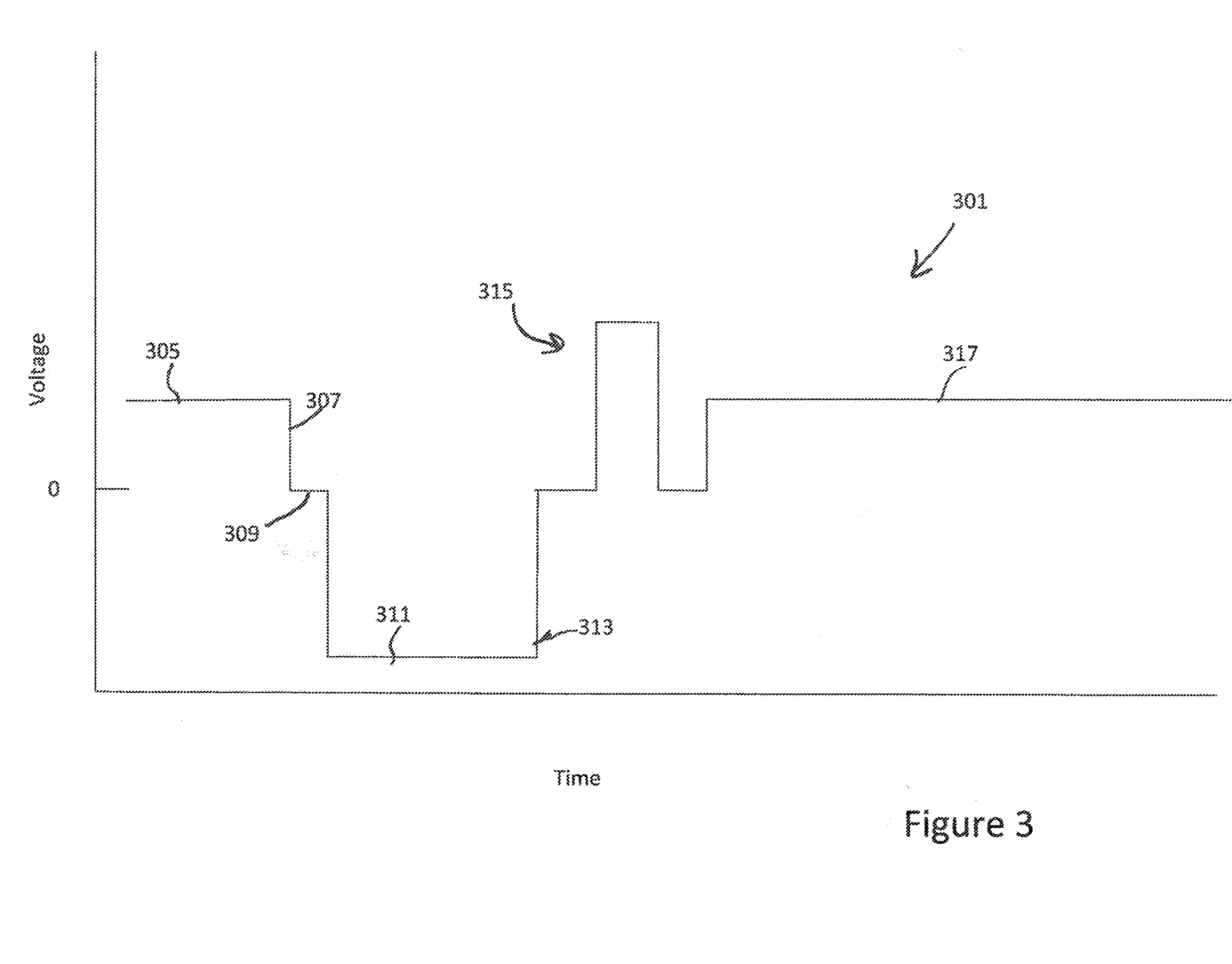
FIG. 3 is a timing diagram depicting an electrophoresis process in accordance with certain embodiments described herein.

In certain embodiments, such as depicted in FIG. 3, the sequence of operations (a timing diagram 301) is as follows:
 a. initiate electrophoresis of a current sample in a capillary;
 b. conduct steady-state transport of DNA fragments from the current sample; this involves applying a constant electrophoresis voltage (operation 305);
 c. before completing electrophoresis of the current sample, halt application of the electrophoresis voltage; this interrupts the steady-state transport of the DNA fragments in the current sample (operation 307);
 d. allow system to rest for a defined period, during which no voltage is applied (operation 309);
 e. apply a reverse polarity voltage to the capillary to drive transport of the DNA fragments in the opposite direction (operation 311);
 f. stop application of the reverse polarity voltage (operation 313);
 g. perform initiation steps for the next sample: introduce the next sample to the inlet region, apply the initial forward voltage pulse to create a plug of the next sample near the inlet of the capillary, end the initiation pulse, flush the sample from the inlet region (operation 315);
 h. apply steady-state running voltage to drive transport of the DNA fragments from the current sample and for the next sample in the electrophoresis capillary (operation 317);
 i. complete the interrogation of the current sample; and
 j. stitch electropherogram traces to eliminate unsteady portions of the process.

Certain embodiments of the reverse pulse interruption electrophoresis process may be understood as follows. By interrupting the migration of a first sample and then reversing the migration for some time before resuming migration at the original conditions, some sample fragments may pass the interrogation location multiple times: first before the interrupt, then secondly when the reverse polarity is applied and lastly again when the original conditions has been regained. This process may be conducted such that migration is occurring at steady-state conditions during the first and last passage, i.e., before the interruption, and after the original condition has been regained. The electrophoresis data up to and including the first passage is uncompromised as well as the electrophoresis data from its last passage to any other species passing later. By simply removing or ignoring any data between the first passage and the last, all the electropherograms obtained under steady-state transport can reconstructed as if the interruption never happened. In such process, the next sample can be injected prematurely to the finishing of the current sample as desired, without compromising the timing information of said first sample.

In certain embodiments, the process interrupts steady-state electrophoresis of the current sample just after a known species that can be unambiguously identified has been detected in the interrogation region. Then, the process reverses the migration to an extent such that both the introduction of the next sample and application of the high voltage pulse can be performed and subsequently a steady-state is reached before the unambiguously identifiable species is detected for the last time. One example an unambiguously identifiable specie is one of the internal lane standards (ILS) such as the 280 bp ILS marker.

3. Characteristics of the Reverse Polarity Voltage Pulse

The reverse polarity voltage pulse begins after a fraction of the current sample fragments have been detected. In some embodiments, as mentioned, it begins immediately or shortly after an easily recognized fragment or internal calibrant is detected. This allows easy joining of electropherogram traces from before and after the reverse polarity pulse. In certain embodiments, the reserve pulse is initiated only after at least about 50% of the fragments have passed the interrogation region.

The reverse polarity voltage pulse terminates after the current sample's undetected fragments have been sent backwards a sufficient distance that when the next sample initiation is performed, all previously undetected fragments from the current sample reach the interrogation region under steady-state conditions (those that are applied via a steady running electrophoresis voltage for the next sample). In other words, all DNA fragments move across the interrogation region under the influence of a steady running electrophoresis voltage, and some of them do so twice; i.e., the reverse voltage pulse builds in some lead time or distance at the interrogation position.

In certain embodiments, the reverse polarity pulse is applied for a duration and at a magnitude sufficient to drive the current sample DNA fragments backwards by a distance such that when they are exposed to the initiation pulse and the sample flushing portions of the next sample's processing, they still have not reached the interrogation region. When they finally do reach the interrogation region, they are again traveling at a steady-state, which allows them and all subsequent fragments to be read properly. In certain embodiments, at least about 5% of the entire electropherogram (for the current sample) is backed up during the reverse pulse. In certain embodiments, at least about 10% of the entire electropherogram (for the current sample) is backed up during the reverse pulse.

As described above, one approach to ensure that the magnitude and duration of the reverse pulse are sufficient involves detecting a particular peak from an internal calibrant during a first pass, then detecting a peak from the same calibrant again during application of the reverse polarity pulse, and finally detecting a third peak from the same calibrant during application of the forward electrophoresis voltage for the next sample.

The negative voltage pulse has a magnitude and duration sufficient to accomplish one or more of the above objectives. If its magnitude is relatively low, it may have to be applied for a relatively longer duration. By contrast, if its magnitude is relatively high, it may be applied at a relatively shorter duration.

The hardware for using a reverse polarity pulse capillary can be similar to existing hardware for capillary electrophoresis. However, in certain embodiments, the hardware employs a power supply that runs in reverse or applies a reverse bias.

Splicing Electropherogram Traces

Figure 4A:
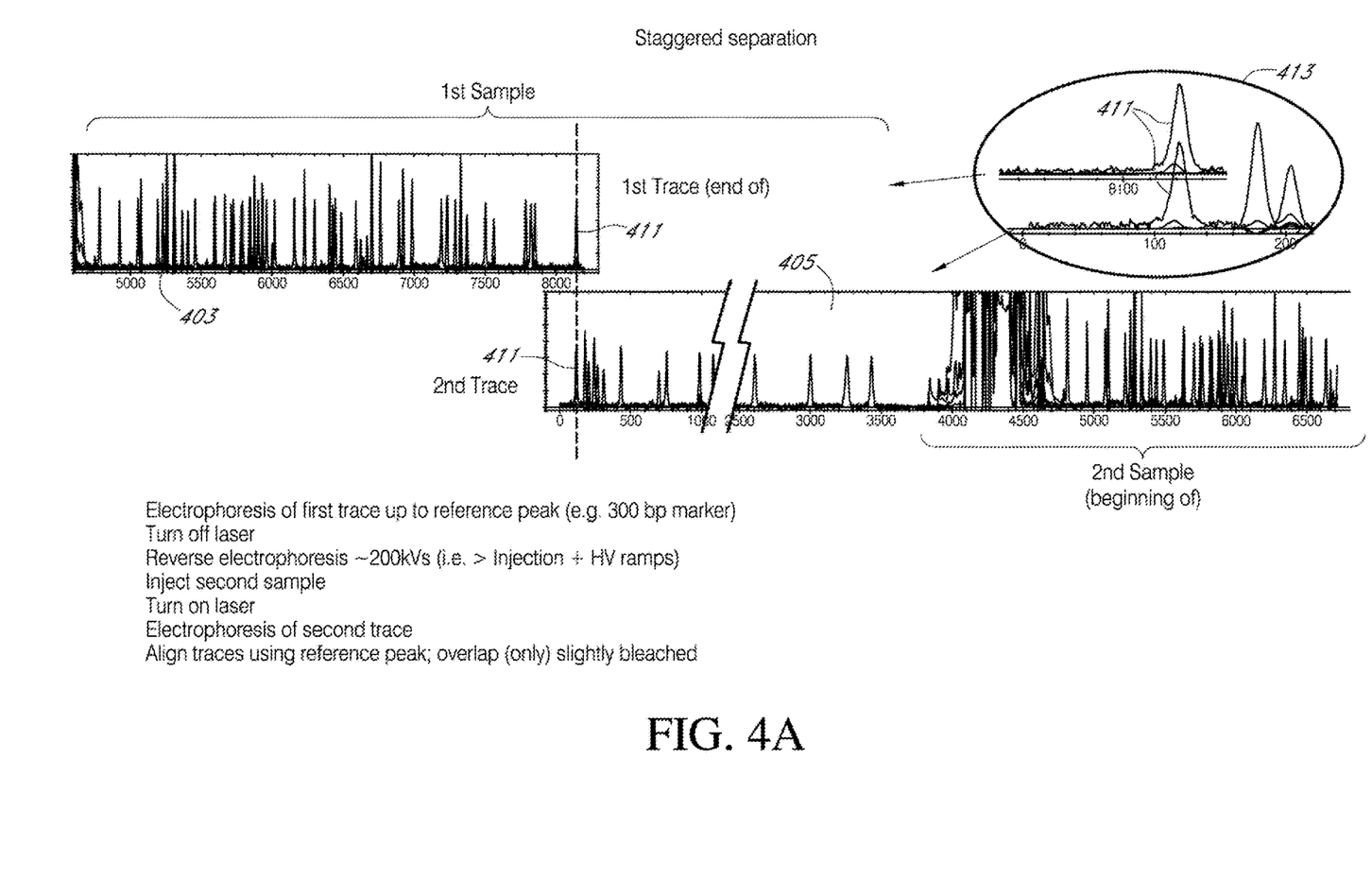
FIG. 4A is a partial electropherogram of two samples provided in two traces.
Figure 4B:
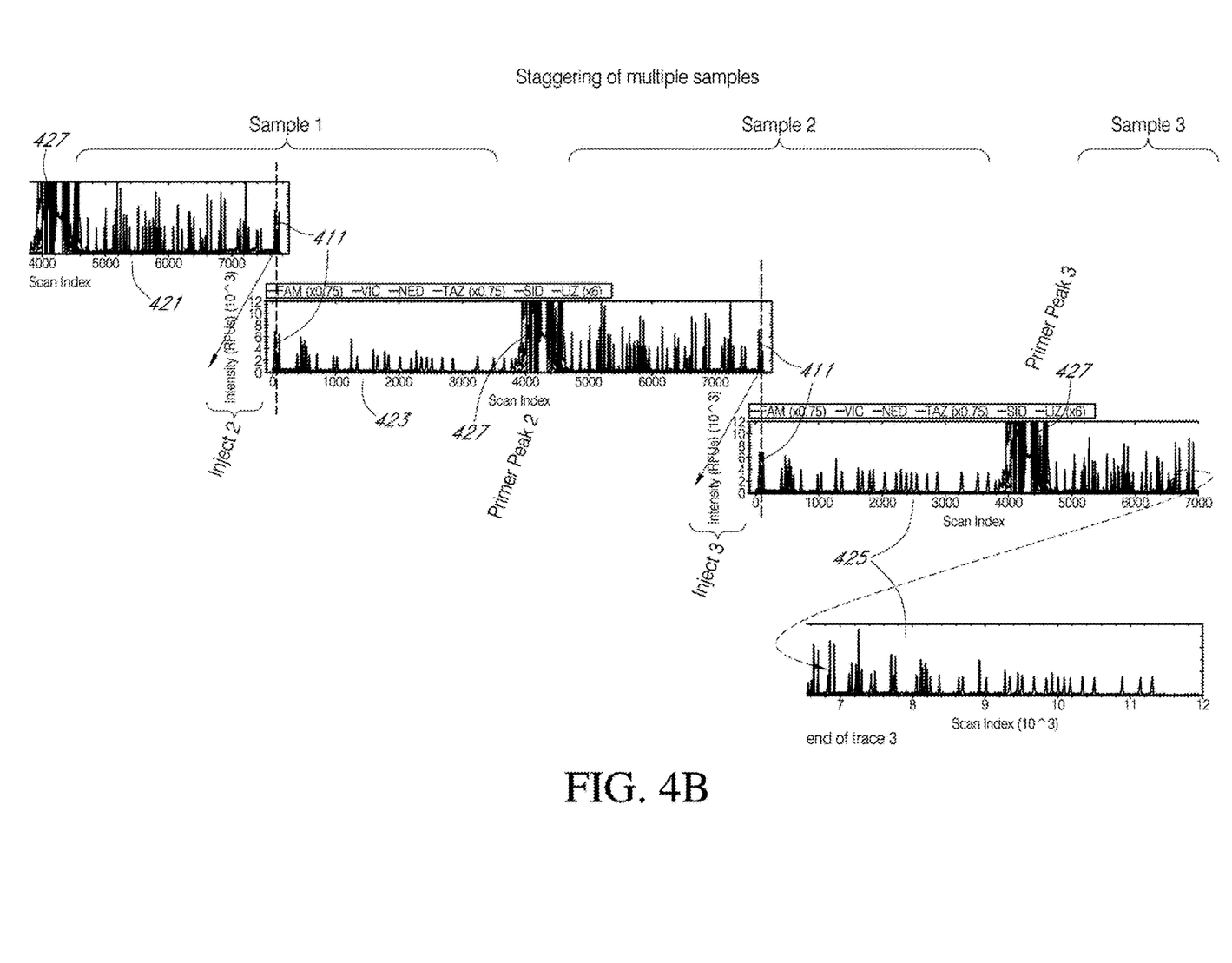
FIG. 4B is a partial electropherogram of three samples provided in three traces.

FIGS. 4A and 4B display the output of a detector during an electrophoresis run in which two DNA-containing samples are successively introduced to the electrophoresis apparatus. The output shows multiple peaks, each associated with a particular DNA fragment passing through an interrogation region of the apparatus. In a color representation, the peaks could be distinguished based on their colors, which correspond to dyes affixed to individual samples or fragments. In FIG. 4A, two traces 403 and 405 are shown, with each one presenting the detector output during constant operation of the detector. The first trace ends when the detector is turned off (or data from the interrogation region is otherwise not collected and/or used). This is a "stop point," which should be distinguished from a "splice point." The second trace begins when the detector is turned on again (or data from the interrogation region is again collected or otherwise used). In the case of samples having their DNA fragments labeled with fluorescent dyes, the laser that stimulates fluorescence of the dyes (in the interrogation region) may be turned off and then on again to end and initiate traces.

In the depicted embodiment, the first trace 403 stops before the DNA fragments of the first or current sample complete their passage through the capillary. Likewise the second trace 405 begins before the fragments of the first sample complete their passage. In between the end of the first trace and the start of the second trace, the voltage of the electrophoresis apparatus changes polarity and runs in reverse. Further, between the two traces, the second sample is loaded and subjected to its injection voltage pulse. In the depicted example, a known DNA fragment peak 411 appears on both traces. This is referred to in the figure as a "reference peak." This may serve as a splice point, as it allows the traces to be "stitched" together to provide effectively one continuous electropherogram. In some embodiments, peak 411 is a known to be present in all samples; e.g., it could be a calibrant peak of a size known to pass through the interrogation region at a time when, or slightly before when, the next sample is to be introduced. Magnified trace segments 413 show how peak 411 can be aligned to stitch together traces 403 and 405 at the proper time point.

The process of depicted example may operate as follows. First the first sample is introduced the inlet region and processed per normal electrophoresis set up (e.g., it is subjected to an injection voltage pulse). The first sample then undergoes steady-state electrophoresis to a point until at least reference peak 411 is recorded. This produces first trace 403. At this point, the process prepares to receive the second sample. It does this by optionally turning off the electropherogram detector (e.g., a fluorescence excitation laser is turned off) and then running electrophoresis in the reverse direction. After running in the reverse for a period sufficient to back up the first sample so that at least some of its fragments will again attain forward steady-state transport before they reach the interrogation region a second time, the second sample is loaded to the inlet region and subjected to an injection voltage pulse. At some point before, on, or shortly after applying the normal running electrophoresis voltage to the second sample, the electrophoresis detector again begins collecting signal (or at least the signal is made available for further processing). In the depicted example, this involves turning on the fluorescence excitation laser. This begins the process of capturing second trace 405.

Thereafter, electrophoresis proceeds as normal, with the first sample completing its run through the interrogation region, and the second sample beginning its run through the interrogation region. To process the detected fragment data, and allow proper interpretation of the first sample, the two traces are aligned on reference peak 411.

FIG. 4B illustrates extension of the process to three samples. Of course, the process can be extended to any number of samples so long as the gel remains undegraded and sufficient reagent is available. FIG. 4B illustrates three separate electropherogram traces, the first one 421 covering a first fraction of the first sample's fragments, the second one 423 covering the remaining fraction of the first sample's fragments together with a first fraction of the second sample's fragments, and the third one 425 covering the remaining fraction of the second sample's fragments together with a first fraction of the third sample's fragments. Of course, there would be at least a fourth trace (not shown) to capture the remaining fraction of the third sample's fragments. Note that each trace contains a reference peak 411 that allows alignment of two successive traces. Note also that each sample includes many primer peaks 427 that are smaller than the allele peaks, so the primer peaks occur earlier in the electropherogram.

Control Systems

Systems provided herein include various computational hardware and software. In some embodiments, a system for sample preparation, processing and analysis (or any other system provided herein) includes a controller with a central processing unit, memory (random-access memory and/or read-only memory), a communications interface, a data storage unit and a display. The communications interface includes a network interface for enabling a system to interact with an intranet, including other systems and subsystems, and the Internet, including the World Wide Web. The data storage unit includes one or more hard disks and/or cache for data transfer and storage. The data storage unit may include one or more databases, such as a relational database. In some cases, the system further includes a data warehouse for storing information, such user information (e.g., profiles) and results. In some cases, the data warehouse resides on a computer system remote from the system. In some embodiments, the system may include a relational database and one or more servers, such as, for example, data servers. The system may include one or more communication ports (COM PORTS), one or more input/output (I/O) modules, such as an I/O interface. The processor may be a central processing unit (CPU) or a plurality of CPU's for parallel processing.

The system may be configured for data mining and extract, transform and load (ETL) operations, which may permit the system to load information from a raw data source (or mined data) into a data warehouse. The data warehouse may be configured for use with a business intelligence system (e.g., Microstrategy®, Business Objects®). It also can be configured for use with a forensic database such as the National DNA Index System (NDIS)) in the USA or NDAD in the United Kingdom, State DNA Index Systems (SDIS), or Local DNA Index Systems (LDIS) or other databases that contain profiles from known and unknown subjects, forensics samples, or other sample types such as organism identifications.

Aspects of the systems and methods provided herein may be embodied in programming. Various aspects of the technology may be in the form of executable code and/or associated data that is carried on or embodied in a type of machine readable medium. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

In some embodiments, the system includes one or more modules for sample processing and/or analysis, and a controller for facilitating sample processing and/or analysis. The controller can include one or more processors, such as a central processing unit (CPU), multiple CPU's, or a multi-core CPU for executing machine-readable code for implementing sample processing and/or analysis. The system in some cases directs a sample sequentially from one module to another, such as from a sample preparation module to an electrophoresis module.

By maximizing the throughput of a single capillary in essence reducing the total time to answer for the last sample, the need for additional capillaries to meet needs for sample to answer is reduced. For example, a single capillary system can serve a plurality of sample preparation modules. Even when all modules have finished preparing a sample at the same time, the time until when the last sample has been fully analyzed is still relatively short.

Systems and methods provided herein, including the components of such systems and various routines of such methods, may be combined with or modified by other systems and methods. In some situations, the above-described systems may be combined or modified by the systems described in U.S. Patent Publication No. 2011/0005932 to Jovanovich et al. ("UNIVERSAL SAMPLE PREPARATION SYSTEM AND USE IN AN INTEGRATED ANALYSIS SYSTEM") ("Jovanovich"), which is entirely incorporated herein by reference in its entirety.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A system for performing capillary electrophoresis of multiple samples, the system comprising:
    a capillary containing a separation medium and comprising an inlet end, a distal end, and an interrogation region between the inlet end and the distal end;
    an inlet in communication with the inlet end of the capillary and configured to receive a plurality of samples containing DNA fragments having a plurality of different sizes;
    a detector configured to detect DNA fragments moving through the interrogation region of the capillary;
    a power source configured to selectively apply forward and reverse polarity voltages between the inlet end and the distal end of the capillary; and
    logic configured to cause execution of the following operations:
        introducing a first sample of the plurality of samples to the inlet end of the capillary, the first sample comprising first DNA fragments having a plurality of different sizes;
        performing electrophoresis on the first sample in the capillary by applying a first substantially constant forward polarity electrophoresis voltage to the capillary while the detector detects some of the first DNA fragments at the interrogation region;
        before all of the first DNA fragments have passed the interrogation region, applying a reverse polarity voltage pulse to the capillary, thereby transporting at least some of the first DNA fragments in the capillary toward the inlet end of the capillary;
        introducing a second sample of the plurality of samples to the inlet end of the capillary, the second sample comprising second DNA fragments having a plurality of different sizes; and
        applying a second substantially constant forward polarity electrophoresis voltage to the capillary to simultaneously perform electrophoresis on the second DNA fragments and the first DNA fragments.

2. The system claim 1, wherein the logic is further configured to cause execution of the following operation:
creating an electropherogram of the first sample by splicing together partial electropherograms of the first sample obtained before and after applying the reverse polarity voltage pulse.

3. The system of claim 2, wherein splicing together comprises removing data obtained after a reference point in a first partial electropherogram obtained before the power source applies the reverse polarity voltage pulse and removing data obtained before the reference point in a second partial electropherogram obtained after the power source applies the reverse polarity voltage pulse.

4. The system claim 1, wherein the logic is further configured to cause execution of the following operation:
amplifying DNA to produce amplicons from loci of short tandem repeats (STRs), the amplicons being the DNA fragments.

5. The system of claim 1, further comprising:
a cartridge comprising fluidic passages and a thermocycler configured to perform polymerase chain reaction.

6. The system of claim 1, wherein the logic is further configured to cause the following operations:
while performing electrophoresis on the first sample in the capillary, detecting, via the detector, for a first time an internal calibrant at the interrogation region;
while the power source applies the reverse polarity voltage pulse to the capillary, detecting, via the detector, for a second time the internal calibrant at the interrogation region; and
while the power sources applies the second substantially constant forward polarity electrophoresis voltage to the capillary, detecting, via the detector, for a third time the internal calibrant at the interrogation region.

7. The system of claim 6, wherein the logic is further configured to cause the following operations:
interpreting the electrophoresis of the first DNA fragments and the second DNA fragments, wherein the interpreting comprises disregarding signal obtained by the detector at the interrogation region during a period between the detector detecting the internal calibrant for the first time and third time.

8. The system of claim 1,
wherein the logic is further configured to cause the introduction of the second sample to the inlet end of the capillary by causing:
introduction of the second sample to an inlet region in contact with the inlet end of the capillary;
application of an injection forward polarity voltage pulse to create a plug of the second DNA fragments proximate the inlet of the capillary; and
flushing of the second sample from the inlet region.

9. The system of claim 1, wherein the logic is further configured to cause the power source to terminate the reverse polarity voltage pulse prior to introducing the second sample to the inlet end of a capillary.

10. The system of claim 1, wherein the logic is further configured to cause the power source to terminate the reverse polarity voltage pulse prior to the power source applying the second substantially constant forward polarity electrophoresis voltage to the capillary.

11. The system of claim 1, wherein the logic is further configured to cause the following operations:
applying, via the power source, a second reverse polarity voltage pulse to the capillary, thereby transporting at least some of the second DNA fragments in the capillary toward the inlet of the capillary;
introducing a third sample of the plurality of samples to the inlet of the capillary, the third sample comprising third DNA fragments having a plurality of different sizes;
applying, via the power source, a third substantially constant forward polarity electrophoresis voltage to the capillary to simultaneously perform electrophoresis on the third DNA fragments and the second DNA fragments.

* * * * *